June 2, 1936. R. E. WILBER Plant Pat. 178
ROSE
Filed Jan. 2, 1936
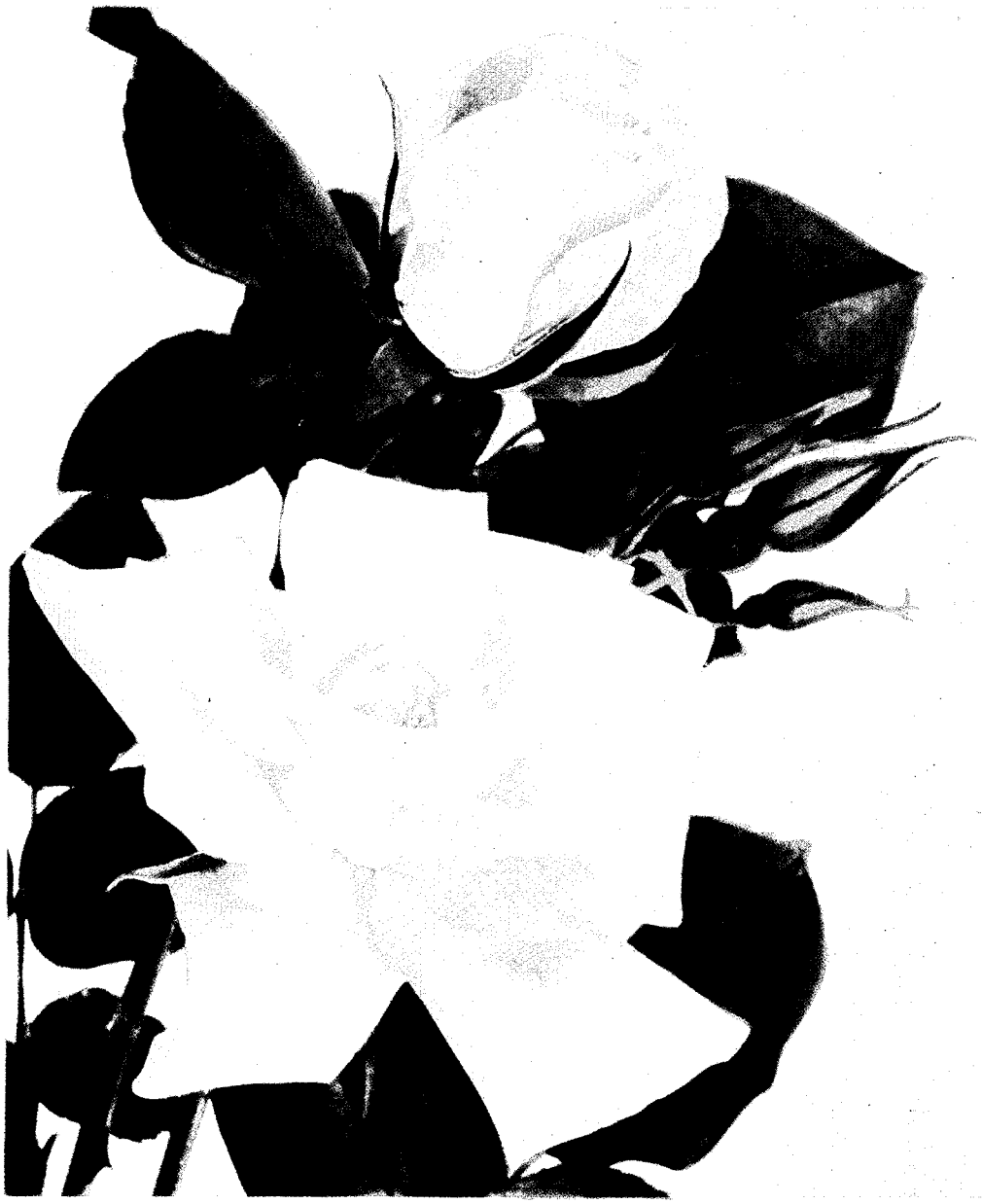
Inventor
Rena Eveline Wilber
By Orville M. Kile
Plant Patent Agent.

Patented June 2, 1936

Plant Pat. 178

UNITED STATES PATENT OFFICE

178

ROSE

Rena Eveline Wilber, Seattle, Wash.

Application January 2, 1936, Serial No. 57,262

1 Claim. (Cl. 47—61)

My present invention relates to improvements in climbing roses. The purpose of my invention is to provide a vigorous climbing rose producing beautiful foliage and flowers of a pleasing color heretofore unknown in a climber or any other type of rose.

My new variety was produced by plant breeding work carried on over a period of fifteen years. First I crossed a Dr. Van Fleet climber with the tea rose Lady Roberts, thereby producing a very hardy climber named "Myra." In 1929, I crossed Myra with the pernetiana Constance Casson. One of the resulting seedlings is the subject of this plant patent application.

The accompanying illustration shows in full color, and in approximately natural size in the original, several tight buds, an opening bud and a fully opened flower, as well as some of the stems and leaves of this variety.

*The flower*

The following description is based on flowers grown in Seattle, Washington in late May and early June.

*Flowers* are borne both singly and in groups of two to three.

*Buds.*—Large, tapering, pointed, about 1½ to 2 inches in length including the hips. Peduncle medium length, smooth, heavy, slightly bending, light green in color, with reddish-brown on side facing sun, hips very prominent.

*Sepals.*—Quite long, 1½ to 1¾ inches and completely enclose the bud since the sepals extend about ¼ inch beyond the end of bud. Color is light green with reddish-brown areas on side facing the sun. Hips rather globular in form.

*Color.*—As the calyx breaks the color is predominantly "peach red" or darker at the top (Ridgway's Color Standards and Nomenclature, Plate I), with increasing amounts of yellow toward the base of the bud, showing first "cadmium orange" (Plate III), and then "cadmium yellow" (Plate III) as the base of the bud is approached. The unfolding bud may even show vermilion on the edges of the petals.

As the first petals open, the cadmium orange is quite prominent, and the peach red appears around the edges of the petals and is suffused over one-third of the area bordering the outer edges of each petal. The cadmium yellow is at this stage confined to the basal portion of the petals surrounding the point of attachment.

*Blossom.*—Size when fully opened is large, measuring 4½ to 5 inches across and often 6 inches on the stronger plants.

*Petalage.*—Double, arranged regularly in three rows. A typical blossom, grown out-of-doors, in the month of June in the latitude of Seattle, has about 15 large petals and two or three small irregular central petals.

*Form.*—Cup-shaped, flat on top, petals rather loosely arranged and non-rolling except in their later stages.

*Petals.*—Rather thick and leathery, ovate, not scalloped or only slightly scalloped.

*Color.*—As the blossom opens one-half to two-thirds, the peach red color gradually changes to a pink, between "geranium pink" and "begonia pink" (Plate I), while the cadmium orange fades to a cadmium yellow. The coloring is not greatly different on the inside surfaces of the petals from that on the outer surfaces, but when viewed from the top, the half to two-thirds opened flower has a decidedly pink appearance. When the blossom reaches full maturity it takes on still lighter tones, the pink becoming approximately "hermosa pink" (Plate I), and the yellow becoming "lemon chrome" (Plate IV) or even lighter.

The flower has good lasting qualities. It is fragrant, having a rather heavy pungent odor.

*Reproductive organs*

*Stamens.*—Many, regularly arranged, large and long, pinkish in color and mounted with large yellowish anthers.

*Pistils.*—Medium number, white, closely bunched in columnar form. Ovary case is large and well formed, protruding somewhat outside the calyx.

*Hips.*—Large, globular, green.

*Sepals.*—1½ to 1¾ inches long, quite prominent, very regular and non-foliaceous in form, edges beset with hair-like projections regularly spaced.

*The plant*

*Foliage.*—Leaves compound, of 5 leaflets, moderately abundant, large in size, leathery texture, the apex leaflet of each compound leaf measuring 3 to 3½ inches in length and 2¼ to 2½ inches in width, ovate in shape and not inclined to curl. Each leaflet has finely serrated edges. The leaves are a beautiful, glossy green, approximately "forest green" (Plate XVII) on their upper surface and a much lighter green, approximately "light elm green" (Plate XVII), on their nether surface. The rachises on the third compound leaf and below usually bear three rather stout thorns on their nether side. Stipules are broad and terminate in sharp, spreading, non-curling points.

*Growth.*—Climbing, and a free grower. New canes grow 7 to 9 feet on ordinary soil and much more in favored locations.

Canes are strong, of brownish-red color on the side facing sun and medium green on other side. Thorns are numerous below the second or third leaf branch, brownish-red in color and pointing either at right angles to stem or upward.

The plant is hardy in the Seattle area except where the ground is very wet. It is strong and vigorous, and apparently disease resistant.

The foliage is highly decorative, the long, pointed buds on stiff brownish stems contrasting with the glossy rich foliage to give a beautiful effect even before blooming.

This variety is a very early bloomer.

*Comparisons*

There is no other rose known to me, either climber or any other type, that bears sufficient resemblance to this rose to permit of comparison. The form of bud and petals somewhat resembles Countess Vandell, but the coloring is entirely different. The color of the bud of my new variety is very much like the bud of Angele Pernet, but the form is different. The full blown flower appears to be entirely unique; I know of nothing with which to compare it.

Having thus disclosed my invention, I claim:

The variety of climbing rose herein described and illustrated, characterized particularly by its vigorous growth, rich glossy foliage, extremely long buds, early blooming habits, and its plentiful production of beautiful large peach and cadmium colored flowers as described.

RENA EVELINE WILBER.